United States Patent [19]

Marhold et al.

[11] Patent Number: 4,611,003

[45] Date of Patent: * Sep. 9, 1986

[54] N-SUBSTITUTED BENZOYL-N'-3,4-TETRAFLUOROETHYLENEDIOXY-UREA PESTICIDES

[75] Inventors: Albrecht Marhold, Leverkusen; Wilhelm Sirrenberg, Sprockhoevel; Erich Klauke, Odenthal; Ingeborg Hammann, Muelheim; Benedikt Becker, Ratingen; Ingomar Krehan, Cologne; Wilhelm Stendel, Wuppertal, all of Fed. Rep. of Germany

[73] Assignee: Bayer Aktiengesellschaft, Leverkusen, Fed. Rep. of Germany

[*] Notice: The portion of the term of this patent subsequent to Aug. 20, 2002 has been disclaimed.

[21] Appl. No.: 503,938

[22] Filed: Jun. 13, 1983

[30] Foreign Application Priority Data

Jun. 24, 1982 [DE] Fed. Rep. of Germany ....... 3223505

[51] Int. Cl.[4] .................... A01N 43/02; C07D 319/14
[52] U.S. Cl. ..................... 514/452; 549/366
[58] Field of Search ................. 549/365, 366; 514/452

[56] References Cited

U.S. PATENT DOCUMENTS 4,103,022  7/1978  Sirrenberg et al. .
4,139,636  2/1979  Sirrenberg et al. .
4,536,587  8/1985  Sirrenberg et al. ................. 549/366

FOREIGN PATENT DOCUMENTS 0042533  12/1981  European Pat. Off. .
2123236  12/1971  Fed. Rep. of Germany .

Primary Examiner—Ethel G. Love
Attorney, Agent, or Firm—Sprung Horn Kramer & Woods

[57] ABSTRACT

Compounds of the formula

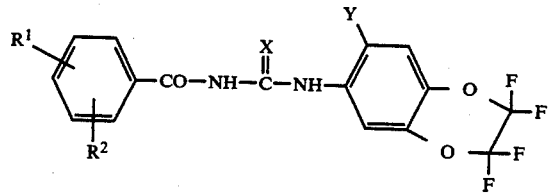

in which
$R^1$ is hydrogen, halogen or alkyl,
$R^2$ is halogen, alkyl or alkylthio,
X is oxygen or sulphur, and
Y is hydrogen, halogen, alkyl or halogenoalkyl,
which possess pesticidal activity.

12 Claims, No Drawings

N-SUBSTITUTED BENZOYL-N'-3,4-TETRAFLUOROETHYLENE-DIOXY-UREA PESTICIDES

The invention relates to new N-fluoroalkylene-dioxy-phenyl-N'benzoyl-(thio)ureas, processes for their preparation and their use as pest-combating agents, in particular as insecticides.

It has already been disclosed that certain benzoyl-ureas, such as, for example, N-(4-chloro-phenyl)-N'-(2,6-difluorobenzoyl)-urea, N-(4-trifluoro-methoxy-phenyl)-N'-(2-chloro-benzoyl)-urea and N-(2,2,4,4-tetrafluoro-1,3-benzodioxin-6-yl)-N'-(2-chloro-benzoyl)-urea, have insecticidal properties (see German Offenlegungsschrift (German Published Specification) No. 2,123,236; U.S. Pat. Nos. 4,139,636 and 4,103,022 and pending U.S. appln. Ser. No. 268,961, filed June 1, 1981, now abandoned.

New substituted N-fluoroalkylenedioxy-phenyl-N'-benzoyl-(thio)ureas of the formula I

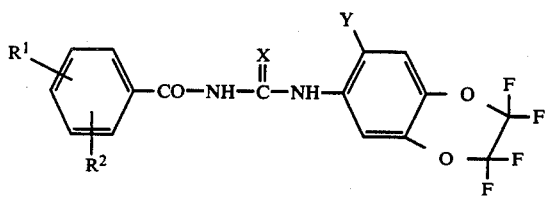

have now been found, in which
$R^1$ represents hydrogen, halogen or alkyl;
$R^2$ represents halogen, alkyl or alkylthio;
X represents oxygen or sulphur; and
Y represents hydrogen, halogen, alkyl or halogenoalkyl.

The new compounds of the formula (I) are obtained in accordance with the invention when (a) substituted benzoyl iso(thio)cyanates of the formula II

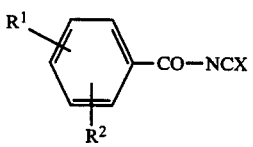

in which
$R^1$, $R^2$ and X have the meanings given above,
are reacted with fluoroalkylenedioxy-anilines of the formula III

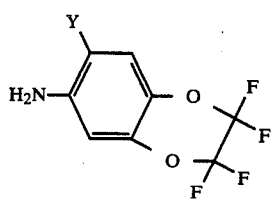

in which
Y has the meaning given above,
if appropriate in the presence of a diluent, or (b) substituted benzamides of the formula IV

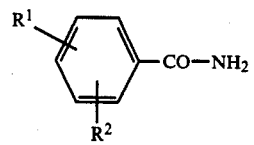

in which
$R^1$ and $R^2$ have the meanings given above,
are reacted with fluoroalkylenedioxy-phenyl iso(thio)cyanates of the formula V

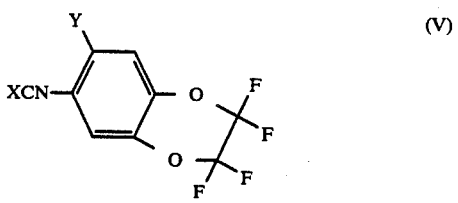

in which
X and Y have the meanings given above,
if appropriate using a diluent, and the resulting end products of the formula I are isolated.

The new compounds of the formula (I) possess properties which make it possible to use them as pest-combating agents; in particular, they are distinguished by outstanding insecticidal activity.

Surprisingly, the N-fluoroalkylenedioxy-phenyl-N'-benzoyl-ureas according to the invention, of the formula (I), exhibit more advantageous properties than the compounds known from the prior art.

In the definition of $R^1$, $R^2$ and Y, alkyl preferably denotes straight-chain or branched alkyl having 1 to 6, preferably 1 to 4, carbon atoms. Methyl, ethyl, n- and i-propyl, n, i- and t-butyl, n-pentyl and n-hexyl may be mentioned. Methyl and ethyl, in particular methyl, may be preferably mentioned.

In halogenoalkyl Y, the alkyl group preferably has the same meaning as in the case of alkyl $R^1$ and Y, it being possible for the alkyl group to be substituted by 1 or more, preferably 1 to 5, in particular 1 to 3, identical or different halogen atoms. The $CF_3$ group is very particularly preferred.

Alkylthio $R^2$ preferably represents alkylthio having 1 to 6, in particular 1 to 4, carbon atoms, methylthio being mentioned.

X preferably represents oxygen.
Y preferably represents hydrogen.

$R^1$ and $R^2$ can assume any desired positions in the phenyl ring. They are preferably in the 2,6-position, 2,5-position, 2,4-position or 3,4-position, in particular in the 2,6- or 2,4- or 2,5-position, very particularly preferably in the 2,6-position. If $R^1$ represents hydrogen, the 2-, 3- and 4-positions are preferred for $R^2$, the 2-position being particularly preferred.

Halogen $R^1$, $R^2$ and Y represent fluorine, chlorine, bromine or iodine, preferably fluorine, chlorine and bromine, in particular fluorine and chlorine.

Preferred compounds of the formula I are those in which the definition of the radicals have the following meanings:
$R^1$ represents hydrogen, halogen or alkyl having 1 to 6 carbon atoms;
$R^2$ represents halogen or alkyl having 1 to 6 carbon atoms;

X represents oxygen or sulphur; and y represents hydrogen, halogen, alkyl having 1 to 6 carbon atoms or halogenoalkyl having 1 to 6 carbon atoms and 1 to 5 halogen atoms, with the exception of that compound in which $R^1$ represents hydrogen, $R^2$ represents 2-fluoro, X represents sulphur and Y represents hydrogen.

The position of $R^1$ and $R^2$ in these compounds corresponds to the above explanations.

In a particular embodiment of the invention, the definition of the radicals in the compounds of the formula (I) has the following meaning:

$R^1$ represents hydrogen, fluorine, chlorine, bromine, iodine or methyl, preferably hydrogen, fluorine or chlorine;

$R^2$ represents fluorine, chlorine, bromine, iodine or methyl, preferably fluorine or chlorine;

X represents oxygen or sulphur, preferably oxygen; and

Y represents hydrogen, chlorine, methyl or trifluoromethyl, preferably hydrogen, with the exception of that compound in which $R^1$ represents hydrogen, $R^2$ represents 2-fluoro, X represents sulphur and Y represents hydrogen.

The position of $R^1$ and $R^2$ in these compounds corresponds to the above explanations.

Among these, particularly preferred compounds of the formula I are those in which $R^1$ represents hydrogen, fluorine or chlorine;

$R^2$ represents fluorine or chlorine;

X represents oxygen; and y represents hydrogen.

The position of $R^1$ and $R^2$ in these compounds corresponds to the above explanations.

If, for example, 2-chloro-benzoyl isocyanate and 3,4-(tetrafluoroethylenedioxy)-aniline are used as starting materials in process (a), and 2,6-fluoro-benzamide and 3,4-(tetrafluoroethylenedioxy)-phenyl isocyanate are used as starting materials in process (b), the corresponding reactions can be represented by the following equations:

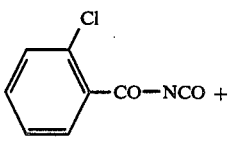
(a)

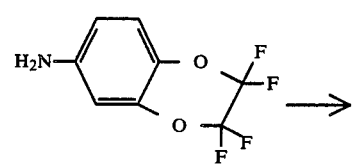

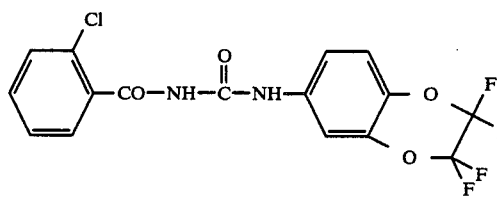

-continued

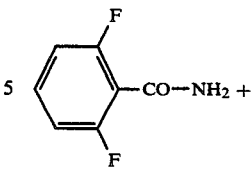
(b)

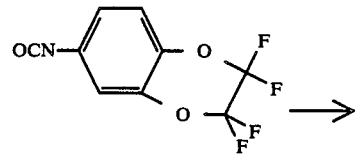

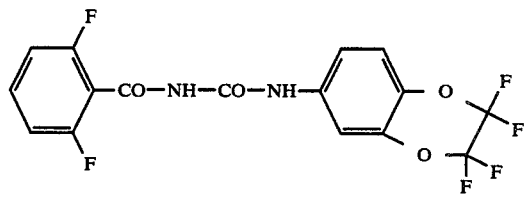

Formulae (II) and (III) or (IV) and (V) give definitions of the starting materials to be used in the preparation processes (a) and (b).

Benzoic acid amides (IV) to be used as starting compounds, and the corresponding benzoyl iso(thio)cyanates (II) are known and can be prepared analogously to known processes, by generally customary methods (see, for example, J. Org. Chem. 30, (1965), 4306–4307 and DE-AS (German Published Specification) No. 1,215,144).

The following may be mentioned as examples: 2-fluoro-, 2-chloro-, 2-bromo-, 2-iodo-, 2-methyl-, 2,6-difluoro-, 2,6-dichloro-, 2,6-dibromo, 2chloro-6-fluoro-, 2-chloro-4-fluoro- and 2-chloro-5-fluorobenzoic acid amide, 2-fluoro-, 2-chloro-, 2-bromo-, 2-iodo-, 2-methyl-, 2,6- difluoro-, 2,6-dichloro-, 2,6-dibromo- and 2-chloro-6-fluoro-, 2-chloro-4-fluoro- and 2-chloro-5-fluorobenzoyl isocyanate and 2-fluoro-, 2-chloro-, 2-bromo-, 2-iodo-, 2-methyl-, 2,6-difluoro-, 2,6-dichloro-, 2,6-dibromo- and 2-chloro-6fluoro-2-chloro-4-fluoro and 2-chloro-5-fluorobenzoyl isothiocyanate.

Fluoroalkylenedioxy-anilines (III) furthermore to be used as starting materials, and the corresponding fluoroalkylenedioxy-phenyl iso(thio)cyanates (V), are likewise known and can be prepared analogously to known processes, by generally customary methods (see German Offenlengungsschrift (German Published Specification) No. 2,848,531).

The following may be mentioned as examples:
6-amino-, 6-isocyanato- and 6-isothiocyanato-2,2,3,3-tetrafluoro-1,4-benzodioxin,
6-amino-, 6-isocyanato- and 6-isothiocyanato-7-chloro-2,2,3,3-tetrafluoro-1,4-benzodioxin, and
6-amino-, 6-isocyanato- and 6-isothiocyanato-7-trifluoromethyl-2,2,3,3-tetrafluoro-1,4-benzodioxin.

The process variants for the preparation of the new N-fluoroalkylenedioxy-phenyl-N'-benzoyl-(thio)ureas are preferably carried out using diluents.

Suitable diluents are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylenesulphone and hexamethylphosphoric acid triamide.

The reaction temperature can be varied within a relatively wide range. In general the reactions are carried out at between 20° and 180° C., preferably at 60° to 120° C. The process variants according to the invention are carried out in general under atmospheric pressure.

To carry out the process variants according to the invention, the starting materials are usually employed in equimolar amounts. An excess of either of the reactants has no substantial advantages. The reaction is carried out in general in a suitable diluent, and the reaction mixture is stirred for several hours at the required temperature. Thereafter, the reaction mixture is allowed to cool and, in the case in which the end products are poorly soluble in the solvent used, is filtered off under suction from the product which has crystallized out. Otherwise, the isolation, and if appropriate, purification, are effected by generally customary methods, for example by evaporating off the solvent (if appropriate under reduced pressure). The compounds are characterized by the melting point, the NMR spectrum and elementary analysis.

As already stated, the present invention, in addition to relating to the new compounds of the formula I and their preparation, also relates to pest-combating agents which contain compounds of the formula I, the preparation of these pest-combating agents and their use. The compounds according to the invention, of the formula I, also exhibit fungicidal activity, a factor which increases their value when they are used as pest-combating agents in plant protection.

The active compounds are well tolerated by plants and are suitable for combating animal pests, especially insects, arachnida and nematodes, very particularly preferably for combating insects, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blatella germanica, Aceta demosticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp., From the order of the Anoplura, for example, *Phyllocera vastatrix*, Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisda tabaci, Trialeurodes vaporariurum, Aphis gossypii, Brevicornyne brassicae, Cryptomyzus ribis, Doralis fabae, Doralis pomi, Eriosoma lanigerum, Hyalopterus arundinis, Macorsiphium avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella auroantii, Aspidiotus haederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neutria, Euproctis chrysorrhoea,* Lymantria spp., *Bucculatrix thurberiella, Phillocnistis citrella,* Argrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris sp., Chilo spp., *Pyrausta nubilalis, Ephestia kuehniella, Calleria mellonella, Cacoecia podana, Capua reticulana, Choristoneura funiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabortica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postuca,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp., From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents. Liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: strongly polar solvents, such as dimethylformamide and dimethylsulphoxide; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites, preferably ectoparasitic insects in the field of livestock husbandry and of livestock breeding.

The active compounds according to the invention are used in a known manner in these fields, such as by oral administration, or by dermal application, for example in the form of dipping, spraying, pouring on and spotting on, and dusting.

The new compounds according to the invention, of the formula I, can accordingly also be particularly advantageously employed in animal husbandry (for example cattle, sheep, pigs and poultry, such as chickens, geese etc.). In a preferred embodiment of the invention, the new compounds are administered orally, if appropriate in suitable formulations (see above) and if appropriate together with the drinking water or feed, to the animals. Since they are eliminated in the faeces in an effective manner, the development of insects in the faeces of the animals may be very simply prevented in this manner. The doses and formulations which are suitable in each case depend in particular on the type and the stage of development of the livestock and also on the intensity of infestation by the insects, and can be readily determined and established by the customary methods. In the case of cattle, the new compounds can be employed in, for example, doses of 0.01 to 1 mg/kg of body weight.

The insecticidal activity of the new compounds according to the invention can be seen from the examples which follow:

EXAMPLE A

Phaedon Larvae Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the larvae have been killed; 0% means that none of the larvae have been killed.

In this test, for example, the compounds No. 1, 2, 3, 4, 5, 6 and 14 showed a destruction of 100% after 10 days, in an experiment at an active compound concentration of 0.01%.

EXAMPLE B

Laphygma Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified periods of time, the destruction in % is determined. 100% means that all the caterpillars have been killed; 0% means that none of the caterpillars have been killed.

In this test, for example, compounds No. 1, 3, 4 and 14 showed a destruction of 100% after 7 days, in an experiment at an active compound concentration of 0.001%.

EXAMPLE C

Heliothis armigera Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soy bean shoots (*Glycine max*) are treated by being dipped into the preparation of the active compound of the desired concentration and are infested with tobacco budworm (*Heliothis armigera*), as long as the leaves are still moist.

After the specified periods of time, the destruction in % is determined. 100% means that all the worms have been killed; 0% means that none of the worms have been killed.

In this test, for example, the compound from Example 5 showed a destruction of 100% after 7 days, in an experiment at an active compound concentration of 0.00016.

EXAMPLE D

Mosquito larvae test

Test animals: *Aedes aegypti*
Solvent: Acetone 99 parts by weight
Emulsifier: Benzylhydroxydiphenyl glycol ether 1 part by weight To produce a suitable preparation of active compound, 2 parts by weight of active compound are dissolved in 1,000 parts by volume of solvent which contains the abovementioned amount of emulsifier. The solution thus obtained is diluted with water to the desired lower concentrations.

The aqueous preparations of active compound of the desired concentration are introduced into glass dishes, and about 25 mosquito larvae are then introduced into each glass dish.

After 21 days, the degree of destruction in % is determined. 100% means that all larvae have been killed. 0% means that no larvae at all have been killed.

In this test, for example, the compounds No. 1, 3, 4 and 5 showed a destruction of 100% in the course of 21 days, in an experiment at dilutions of $10^{-3}$ to $10^{-4}$ ppm.

EXAMPLE E

Test with Lucilia cuprina res. Larvae

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm² of horse muscle and 0.5 ml of the preparation of active compound. After 24 hours, the degree of destruction is determined.

In this test, for example, the compounds No. 1, 2, 3, 4, 5 and 6 showed degrees of destruction between 50 and 100%, in an experiment at an active compound concentration of 100 ppm.

The preparation examples which follow are intended to illustrate the preparation of the compounds according to the invention, of the formula I:

EXAMPLE 1

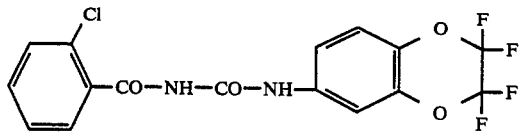

4.6 g of 7-amino-2,2,3,3-tetrafluorobenzo-1,4-dioxene are dissolved in 60 ml of dry toluene, and 3.64 g of 2-chlorobenzoyl isocyanate are added at 60° C., in the absence of moisture. The mixture is stirred for one hour at 80° C. and then cooled to room temperature. The precipitated product is filtered off under suction and dried in vacuo. 8 g of 1-(2-chlorobenzoyl)-3-(2,2,3,3-tetrafluorobenzo-1,4-dioxen-yl)urea of melting point 198° C. are obtained.

Compounds in the tables below are obtained analogously:

TABLE I

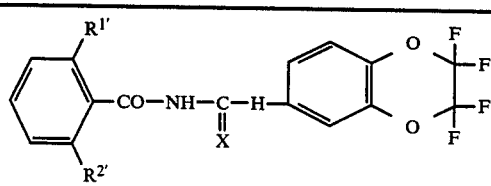

| Example No. | $R^{1'}$ | $R^{2'}$ | X | M.p. (°C.) |
| --- | --- | --- | --- | --- |
| 2 | Cl | Cl | O | 202 |
| 3 | Cl | F | O | 197 |
| 4 | H | Br | O | 199 |
| 5 | F | F | O | 207 |

TABLE I-continued

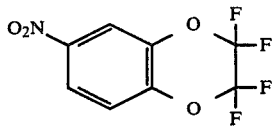

| Example No. | R¹' | R²' | X | M.p. (°C.) |
|---|---|---|---|---|
| 6 | H | F | O | 169 |
| 7 | H | C₂H₅ | O | 137 |
| 8 | H | SCH₃ | O | 197 |
| 9 | F | F | S | 189 |
| 10 | Cl | F | S | 203 |
| 11 | H | Br | S | 172 |
| 12 | H | CH₃ | S | 154 |
| 13 | Cl | Cl | S | 208 |

TABLE II

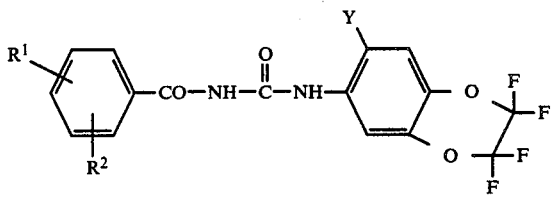

| Example No. | R¹' | R²' | X | M.p. (°C.) |
|---|---|---|---|---|
| 14 | 2-Cl | 4-F | O | 157 |
| 15 | 2-Cl | 5-F | O | 182 |
| 16 | H | 3-Cl | O | 194 |
| 17 | H | 4-Cl | O | 224 |
| 18 | 3-Cl | 4-Cl | O | 197 |

The example which follows is intended to illustrate the preparation of the starting compounds of the formula (II) (Y=hydrogen)

Stage 1

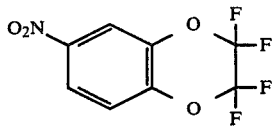

250 ml of hydrogen fluoride, 3 ml of antimony pentachloride and 330 g of 7-nitro-2,2,3-trifluoro-3-chlorobenzo-1,4-dioxene are initially introduced into a VA stainless steel autoclave equipped with a stirrer+reflux condenser, nitrogen is forced in until the pressure is 3 bar, and the mixture is then heated to 125° C. The hydrogen chloride formed is released, at 20 bar, via a control valve under reflux. After a reaction time of 10 hours, the excess hydrogen fluoride is distilled off and the residue is subjected to steam distillation. 265 g of product ($n_D^{20}$: 1.4821), which according to gas chromatographic analysis consists of 79% of 7-nitro-2,2,3,3-tetrafluoro-benzo-1,4-dioxene and 21% of starting material, are obtained. By fractional distillation, pure 7-nitro-2,2,3,3-tetrafluorobenzo-1,4-dioxene of b.p.: 98°-100° C./16 mbar and refractive index $n_D^{20}$: 1.4750 is obtained.

Stage 2

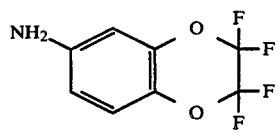

In a hydrogenation apparatus, 52 g of 7-nitro-2,2,3,3-tetrafluorobenzo-1,4-dioxene in 180 ml of methanol are hydrogenated in the presence of 5 g of Raney nickel, at 25°-45° C., with hydrogen at 30-50 bar. After the pressure has been released, the catalyst is filtered off and the solution is distilled. 40 g of 7-amino-2,2,3,3-tetrafluorobenzo-1,4-dioxene of melting point 32° C. are obtained at b.p.: 95°-97° C./ 16 mbar.

The remaining starting materials can be obtained as described above, by generally customary methods and processes.

It will be appreciated that the instant specification and examples are set forth by way of illustration and not limitation, and that various modifications and changes may be made without departing from the spirit and scope of the present invention.

We claim:

1. A compound of the formula

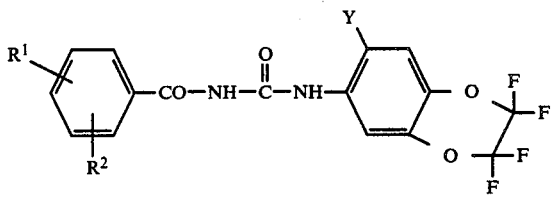

in which
R¹ is hydrogen, halogen, alkylthio or alkyl,
R² is halogen, and
Y is hydrogen, halogen, alkyl or halogenoalkyl.

2. A compound according to claim 1, in which
R¹ is hydrogen, halogen or alkyl having 1 to 6 carbon atoms,
R² is halogen, and
Y is hydrogen, halogen, alkyl having 1 to 6 carbon atoms or halogenoalkyl having 1 to 6 carbon atoms and 1 to 5 halogen atoms.

3. A compound according to claim 2, in which
R¹ is hydrogen, fluorine, chlorine, bromine, iodine or methyl,
R² is fluorine, chlorine, bromine or iodine, and
Y is hydrogen, chlorine, methyl or trifluoromethyl.

4. A compound according to claim 1, in which
R¹ is hydrogen, fluorine or chlorine,
R² is fluorine or chlorine, and
Y is hydrogen.

5. A compound according to claim 1, wherein such compound is 1-(2-chlorobenzoyl)-3-(2,2,3,3-tetrafluorobenzo-1,4-dioxen-yl)-urea of the formula

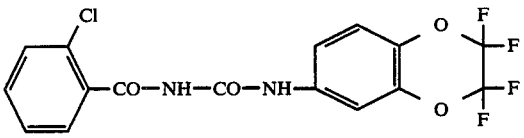

6. A compound according to claim 1, wherein such compound is 1-(2-chloro-6-fluorobenzoyl)-3-(2,2,3,3-tetrafluorobenzo-1,4-dioxen-yl)-urea of the formula

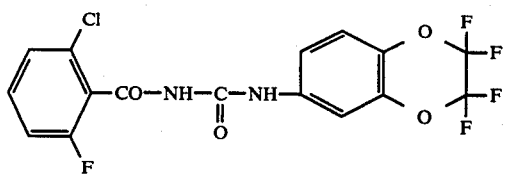

7. A compound according to claim 1, wherein such compound is 1-(2-bromobenzoyl)-3-(2,2,3,3-tetrafluorobenzo-1,4-dioxen-yl)-urea of the formula

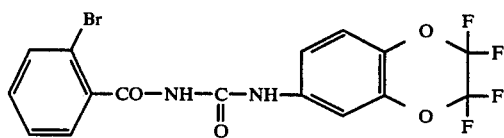

8. A compound according to claim 1, wherein such compound is 1-(2,6-difluorobenzoyl)-3-(2,2,3,3-tetrafluorobenzo-1,4-dioxen-yl)-urea of the formula

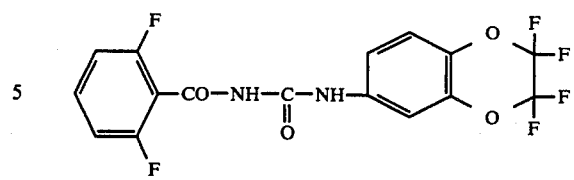

9. A compound according to claim 1, wherein such compound is 1-(2-chloro-4-fluorobenzoyl)-3-(2,2,3,3-tetrafluorobenzo-1,4-dioxen-yl)-urea of the formula

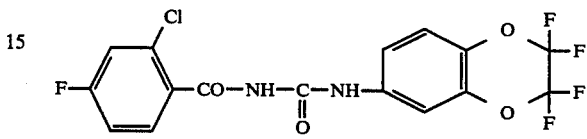

10. A pesticidal composition comprising a pesticidally effective amount of a compound according to claim 1 in admixture with a diluent.

11. A method of combating pests which comprises applying to the pests or to a pest habitat a pesticidally effective amount of a compound according to claim 1.

12. The method according to claim 11, wherein such compound is
1-(2-chlorobenzoyl)-3-(2,2,3,3-tetrafluorobenzo-1,4-dioxen-yl)urea,
1-(2-chloro-6-fluorobenzoyl)-3-(2,2,3,3-tetrafluorobenzo-1,4-dioxen-yl)-urea,
1-(2-bromobenzoyl)-3-(2,2,3,3-tetrafluorobenzo-1,4-dioxen-yl)-urea,
1-(2,6-difluorobenzoyl)-(2,2,3,3-tetrafluorobenzo-1,4-dioxen-yl)-urea or
1-(2-chloro-4-fluorobenzoyl)-3-(2,2,3,3-tetrafluorobenzo-1,4-dioxen-yl)-urea.

* * * * *